United States Patent [19]

Bartlett et al.

[11] Patent Number: 4,585,577

[45] Date of Patent: Apr. 29, 1986

[54] AEROSOL PROPELLANTS OF MONOCHLORODIFLUOROMETHANE, DIMETHYLETHER AND METHYLENE CHLORIDE

[75] Inventors: Philip L. Bartlett; John J. Daly, Jr.; John D. Sterling, Jr., all of Wilmington, Del.

[73] Assignee: E. I. Du Pont de Nemours and Company, Wilmington, Del.

[21] Appl. No.: 560,728

[22] Filed: Dec. 12, 1983

[51] Int. Cl.$^4$ .................. C09K 3/30; C11D 17/00; A61L 9/04
[52] U.S. Cl. .................. 252/305; 252/10; 252/90; 424/45; 424/47; 424/76; 424/DIG. 1
[58] Field of Search .................. 252/305, 90, 10; 424/45, 47, 76, DIG. 1

[56] References Cited

U.S. PATENT DOCUMENTS

| | | | |
|---|---|---|---|
| 2,959,325 | 11/1960 | Beard, Jr. | 222/1 |
| 3,590,006 | 6/1971 | Page et al. | 252/305 X |
| 3,910,848 | 10/1975 | Froehlich et al. | 252/90 |
| 3,922,228 | 11/1975 | Hutchinson | 252/305 X |
| 4,062,795 | 12/1977 | Hutchinson | 252/305 X |
| 4,145,411 | 3/1979 | Mende | 424/45 |
| 4,152,416 | 5/1979 | Spitzer et al. | 424/45 X |
| 4,174,295 | 11/1979 | Bargigia et al. | 424/47 X |
| 4,198,313 | 4/1980 | Bargigia et al. | 424/45 X |
| 4,382,078 | 5/1983 | Berkhoff et al. | 424/45 |
| 4,444,745 | 4/1984 | Jacobson | 424/45 |

OTHER PUBLICATIONS

"Solvay Methylene Chloride", Advertisement, Soap & Chem. Specialties, 33:5, May 1957, p. 73.
Derwent Abstract of Japanese Patent 53086688, (Jan. 1977).
Derwent Abstract of Japanese Patent 54033880, (Aug. 1977).

Primary Examiner—Edward A. Miller
Assistant Examiner—Catherine S. Kilby

[57] ABSTRACT

Propellant gas compositions for aerosol products are disclosed consisting essentially of monochlorodifluoromethane, dimethyl ether and methylene chloride, said compositions having a vapor pressure of about 50 to 60 psig at 70° F.

4 Claims, 1 Drawing Figure

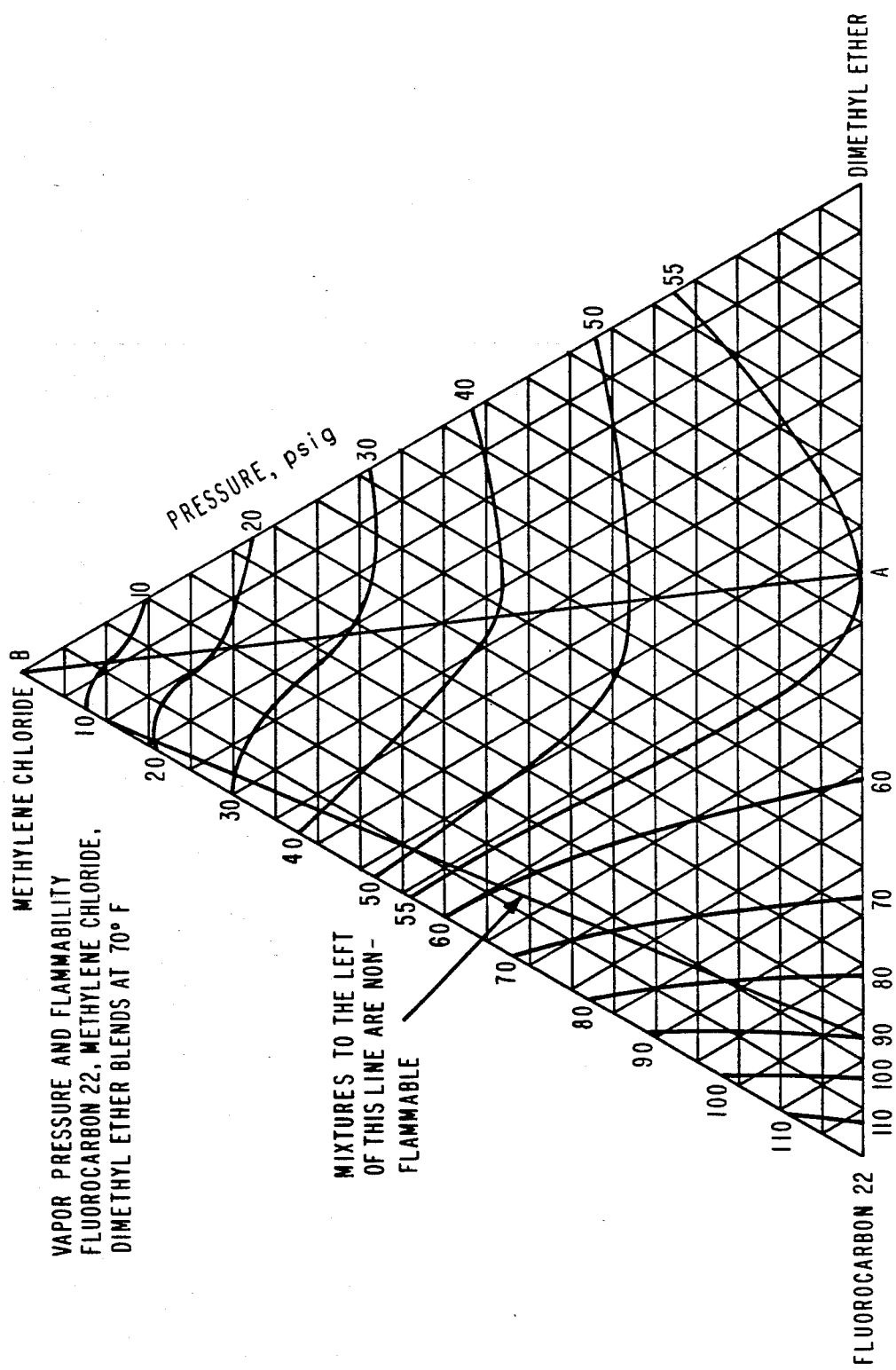

4,585,577

AEROSOL PROPELLANTS OF MONOCHLORODIFLUOROMETHANE, DIMETHYLETHER AND METHYLENE CHLORIDE

BACKGROUND OF THE INVENTION

1. Field of the Invention

This invention relates to propelling gas systems for aerosol products.

2. Description of the Prior Art

Many products designed for household, personal or industrial use are available as aerosol products. Typical examples of such products and ones in which the propellant system of the present invention can be used include personal products such as hair sprays; household products such as paint removers and insecticides; industrial products such as penetrating oils and metal-cleaning sprays; and agricultural products such as tick and flea repellants. All such products utilize the pressure of a propellant gas or a mixture of propellant gases (i.e., a propellant gas system) to expel the active ingredients from the container. For this purpose, most aerosols employ liquified gases which vaporize and provide the pressure to propel the active ingredients when the valve on the aerosol container is pressed open.

An important physical property associated with the dispensing of aerosol products is the vapor pressure of the propellant. Vapor pressure from the viewpoint of this invention is the pressure exerted when a liquified propellant gas is in equilibrium with its vapor in a closed container, such as an aerosol can. Vapor pressure can be measured by connecting a pressure gauge to the valve on an aerosol can or gas cylinder containing the vapor/liquid mixture. A standard of measurement of vapor pressure in the U.S. aerosol industry is pounds per square inch gauge (psig) with the gas/liquid mixture at constant temperature, most commonly at 70° F. When vapor pressure is mentioned in the ensuing specification without reference to temperature, it can be assumed that the pressure is determined at 70° F. The vapor pressures of liquified gases most widely employed as aerosol propellants will vary over the range of about 20 to 90 psig at 70° F. However, for a great many aerosol products, propellants with a vapor pressure in the range of about 50 to 60 psig are most desirable. The propellant systems of the present invention have vapor pressures in this latter range.

SUMMARY OF THE INVENTION

The present invention pertains to aerosol propellant compositions containing the azeotrope of monochlorodifluoromethane and dimethyl ether (DME). This azeotrope which consists of 40% by weight of monochlorodifluoromethane (most commonly referred to in the industry as fluorocarbon 22 or FC-22) and 60% by weight of dimethyl ether is a maximum boiling (−9° F.) minimum vapor pressure (55 psig at 70° F.) azeotrope. It has been found that this azeotrope in admixture with methylene chloride produces useful aerosol propellants with a vapor pressure in the range of about 50 to 60 psig over a relatively wide range of proportions with respect to the amount of methylene chloride present. Methylene chloride can be used with the azeotrope in amounts of about 1–28% by weight, based on the total propellant composition, and the vapor pressure of the propellant gas mixture is still within the desired range of about 50 to 60 psig. A preferred range of methylene chloride concentration is 10–20% by weight of the total propellant gas composition.

Referring to the drawing, the diagram shown is a triangular coordinate chart of the type commonly used in the aerosol industry to illustrate the relationship of concentration and vapor pressure for 3-component systems. This particular chart pertains to the 3-component system consisting of FC-22, dimethyl ether and methylene chloride. A concentration of 100% by weight of a particular component is at the vertex of the triangle where the name of the component appears. A concentration of zero percent of this same component is on the side of the triangle opposite this vertex. A composition representing 33⅓% by weight of each component is at the center of the triangle. The parallel lines leading away from each vertex are spaced at 5 weight percent intervals. The curved lines within the triangle with the same number appearing at each end of the line indicate the makeup of formulations of the three components that exert a vapor pressure designated by the number at the end of the line. These lines are the result of measuring the vapor pressure of a large number of specific compositions until sufficient data points are obtained to accurately draw each vapor pressure line. Each of these vapor pressure lines represents one particular pressure. There is also shown on the chart a line AB extending from the base of the triangle at the point (40/60) representing the composition of the FC-22/DME azeotrope to the apex of the triangle at point B which represents 100% methylene chloride. Determination of the vapor pressure of any given composition comprising the azeotrope and methylene chloride can be quickly ascertained by locating the point on this line in the chart that corresponds to the methylene chloride content of the mixture. The vapor pressure line in closest proximity to this point enables one to closely estimate the vapor pressure of the given composition. Further, it will be apparent from looking at the vapor pressure lines that cross line AB, that about 1 to 28% methylene chloride can be mixed with the azeotrope to produce compositions with vapor pressures that stay within the range of about 50 to 60 psig.

While the preferred mixtures of FC-22 dimethyl ether and methylene chloride are those in which the ratio of FC-22 to dimethyl ether corresponds to the azeotrope of these two components (i.e., a 40:60 ratio of FC-22 to DME), it can be seen from the triangular coordinate chart that vapor pressures within the range of about 50 to 60 psig can also be obtained in three-component mixtures where the ratio of FC-22 to DME falls on either side of the azeotrope. For example, 1–28% methylene chloride can be added to a 50/50 mixture of FC-22 and DME and to a 30/70 mixture of FC-22 and DME without substantially modifying the vapor pressure of the azeotrope. Thus, the broad embodiment of this invention comprises three-component compositions of FC-22, dimethylether and methylene chloride in which the vapor pressure is in the range of about 50 to 60 psig. This would include compositions in which the ratio of FC-22 and DME components are in the ratio of 40:60 and those in which the FC-22/DME is outside this ratio but within the specified vapor pressure range. The proportion of components in such composition can be ascertained from the drawing.

The tendency for little variation in vapor pressure over a relatively wide range of compositions is considered to be unexpected. The present invention involves, in essence, the incorporation of an additional component (methylene chloride) with the FC-22/dimethyl ether azeotrope. Since an azeotrope behaves in liquid/vapor equilibrium as if it were a single compound, it might be expected that with the addition of appreciable quantities of a third component, the vapor pressure of the admixture would be somewhere in the middle area between that of the azeotrope and the third component. However, within the defined limits of the present invention there is essentially little change from the vapor pressure of the azeotrope itself.

The vapor pressure of the FC-22/DME azeotrope is in a desirable range for aerosol propellants. Surprisingly, the addition of methylene chloride, a lower vapor pressure material, in accordance with this invention does not substantially lower the vapor pressure of the system. At the same time, this incorporation of methylene chloride contributes several advantages as described below.

The presence of methylene chloride contributes lower flammability characteristics to the composition as compared to the FC-22/dimethyl ether (40/60) azeotrope. Thus, methylene chloride has a lower explosion limit (LEL) in air of 13.4 vol. %, whereas the FC-22/dimethyl ether (40/60) azeotrope has a LEL in air of 4.3 vol. %. The lower the LEL, the greater is the flammability hazard of a propellant system. Other widely used propellants such as propane, butane and isobutane are even more flammable than methylene chloride, having LELs in air of 1.8–2.2 vol. %.

Certain ratios of the components of the gas mixtures of this invention may be flammable (the area to the right of the flammability line in the drawing), and explosion-proof equipment should be used in loading aerosol cans. However, the presence of methylene chloride in the mixture, together with FC-22 which is nonflammable, will reduce the flammability of many aerosol products to such a degree that special labeling is not required under the Federal Hazardous Substances Act.

In addition to reducing the flammability of the FC-22/DME (40/60) azeotrope, methylene chloride adds increased solvent properties in terms of dissolving aerosol formulation active ingredients. Thus, the Kauri-Butanol number for methylene chloride is about 136, whereas the Kauri-Butanol number for the FC-22/dimethyl ether (40/60) azeotrope is about 46. The higher the Kauri-Butanol number, the better the solvent power is for a compound or mixture of compounds. The Kauri-Butanol numbers for hydrocarbon propellants such as propane, butane and isobutane are about 30.

Finally, because of its relatively low cost, methylene chloride contributes to the economic attractiveness of the propellant. In summary, these ternary compositions enable producers of aerosol products the opportunity to prepare aerosol formulations wherein propellant solvency characteristics, low flammability, and cost can be adjusted without substantial change in vapor pressure.

EXAMPLES

The following examples are typical of the aerosol propellant systems of the present invention and their use in aerosol products. These examples are presented for purposes of illustration only, and are not intended as a limitation on the scope of the invention as described herein.

Procedure

Examples 1 and 2 were prepared using the following procedure. The active ingredients were weighed into a six-ounce three-piece aerosol can 2⅛" in diameter and 4⅜" long. The can was purged with dichlorodifluoromethane (FC-12) vapor to displace the air in the container. The aerosol can valve was then placed into the can and crimped. The propellants were introduced into the can as liquids through the aerosol valve. Volume amounts corresponding to the weight of the propellants were calculated prior to loading, and a glass, calibrated, pressure buret was used to measure and transfer the liquids from storage cylinders to the can. A nitrogen gas pressure of 100 psig was applied to the buret to aid in transferring the liquids from the buret to the can. After the propellant was loaded, the can was weighed, and the weight of propellant recorded. The loaded can was placed in a 70° F. water bath for 30 minutes and the pressure was then measured with a pressure gauge. Also included in the examples is the vapor pressure for the propellant mixtures without active ingredients. The values were obtained from the triangular chart in the drawing. The flame extension and flashback tests were conducted by spraying the samples across a candle flame from a distance of six inches and recording how far the flame extended beyond the candle and how far it flashed back towards the can.

EXAMPLE 1

An illustration of a system useful as an insecticide is as follows:

| Formulation | Wt. % of Propellant | Wt. % of Total Ingredients | Grams/Can |
|---|---|---|---|
| Active Ingredients | | | |
| Natural Pyrethrins | — | 2.0 | 2.0 |
| Piperonyl Butoxide | — | 1.0 | 1.0 |
| Propellants | | | |
| FC-22 | 29.7 | 28.9 | 29.0 |
| DME | 44.6 | 43.2 | 43.4 |
| Methylene Chloride | 25.7 | 24.9 | 25.0 |
| Vapor Pressure of Propellant (psig at 70° F.) | | 51 | |
| Vapor Pressure of filled can (psig at 70° F.) | | 48 | |
| Flame Extension (inches) | | 5 Intermittent | |
| Flashback (inches) | | 0 | |
| Valve | Precision Valve | | |
| Body (inches) | .080 | | |
| Stem (inches) | .018 | | |
| Actuator (inches) | .018 | | |

EXAMPLE 2

Another illustration of a system useful as an insecticide is as follows:

| Formulation | Wt. % of Propellant | Wt. % of Total Ingredients | Grams/Can |
|---|---|---|---|
| Active Ingredients | | | |
| Natural Pyrethrins | — | 2.0 | 2.0 |
| Piperoyl Butoxide | — | 1.0 | 1.0 |
| Kerosene | — | 10.0 | 10.1 |
| Propellants | | | |
| FC-22 | 30.0 | 26.1 | 26.3 |
| DME | 44.9 | 39.1 | 39.4 |
| Methylene Chloride | 25.1 | 21.8 | 22.0 |
| Vapor Pressure of Propellant (psig at 70° F.) | | 51 | |
| Vapor Pressure of filled can | | 46 | |

-continued

| | |
|---|---|
| (psig at 70° F.) | |
| Flame Extension (inches) | 11 |
| | Intermittent |
| Flashback (inches) | 0 |
| Valve | Precision Valve |
| Body (inches) | .080 |
| Stem (inches) | .018 |
| Actuator (inches) | .018 |

We claim:

1. An aerosol propellant composition consisting essentially of monochlorodifluoromethane and dimethyl ether where the monochlorodifluoromethane to dimethylether weight ratio is from 50:50 to 30:70, in admixture with methylene chloride, said composition having a vapor pressure in the range of about 50–60 psig at 70° F.

2. An aerosol propellant composition consisting essentially of an azeotrope of monochlorodifluoromethane and dimethyl ether in a monochlorodifluoromethane:dimethyl ether weight ratio of 40:60 in admixture with methylene chloride, the proportion of the azeotrope to methylene chloride being such that the vapor pressure of the mixture is in the range of about 50–60 psig at 70° F.

3. The composition of claim 2 in which methylene chloride constitutes 1–28% by weight of the propellant composition.

4. The composition of claim 3 in which the methylene chloride is present in an amount of about 10–20% by weight.

* * * * *